United States Patent [19]

Kruper, Jr.

[11] Patent Number: 5,064,956

[45] Date of Patent: Nov. 12, 1991

[54] PROCESS FOR PREPARING MONO-N-ALKYLATED POLYAZAMACROCYCLES

[75] Inventor: William J. Kruper, Jr., Sanford, Mich.

[73] Assignee: The Dow Chemical Company, Midland, Mich.

[21] Appl. No.: 549,791

[22] Filed: Jul. 9, 1990

Related U.S. Application Data

[63] Continuation-in-part of Ser. No. 289,163, Dec. 22, 1988, abandoned, which is a continuation-in-part of Ser. No. 65,739, Jun. 24, 1987, Pat. No. 4,994,560, and a continuation-in-part of Ser. No. 211,496, Jun. 24, 1988, abandoned, and a continuation-in-part of Ser. No. 370,956, Jun. 21, 1989.

[51] Int. Cl.$^5$ .................. C07D 273/00; C07D 257/02; C07D 255/02
[52] U.S. Cl. ...................................... 540/474; 540/467
[58] Field of Search .............................. 540/474, 467

[56] References Cited

FOREIGN PATENT DOCUMENTS 0232751 of 1984 European Pat. Off. .
3014780A 1/1988 Japan .

OTHER PUBLICATIONS

T. A. Kaden, Top Curr. Chem. 121, 157–179 (1984).
M. Studer et al., Helv. Chim. Acta. 69, 2081–2086 (1986).
E. Kimura et al., J. Chem. Soc. Chem. Commun., 1158–1159 (1986).
F. Wagner et al., Inorg. Chem. 15, 408–417 (1976).
P. S. Pallavincini et al., J. Amer. Chem. Soc., 109, 5139–5144 (1987).

Primary Examiner—David B. Springer
Attorney, Agent, or Firm—Duane C. Ulmer; Ronald G. Brookens

[57] ABSTRACT

The invention relates to a novel process to prepare selectively mono-N-alkylated polyazamacrocycles which requires an electrophile with between about one and five equivalents of a suitable macrocycle in a solvent which will not promote a proton transfer.

22 Claims, No Drawings

PROCESS FOR PREPARING MONO-N-ALKYLATED POLYAZAMACROCYCLES

CROSS REFERENCES TO RELATED APPLICATIONS

This application is a continuation-in-part of our co-pending application Ser. No. 289,163, filed Dec. 22, 1988, abandoned; our co-pending application Ser. No. 65,739 filed June 24, 1987, U.S. Pat. No. 4,994,560, our co-pending application Ser. No. 211,496 filed June 24, 1988, abandoned, and of our co-pending application Ser. No. 370,956 filed June 21, 1989.

BACKGROUND OF THE INVENTION

The present invention relates to a process for preparing mono-N-alkylated polyazamacrocycles.

T. A. Kaden, *Top. Curr. Chem.* 121, 157–75 (1984) has shown that simple alkylative techniques using electrophiles and polyazamacrocycles for the production of mono-N-functionalized polyazamacrocyles result in the formation of a mixture of mono, bis, and tris alkylated products which are difficult to separate and purify. To overcome this problem, large excesses of macrocycle, for example 5–10 equivalents relative to electrophile, have been employed by M. Studer et al., *Helv. Chim. Acta.* 69, 2081–86 (1986), by E. Kimura et al., *J. Chem. Soc. Chem. Commun.* 1158–59 (1986), and by Toyo Soda, (inventor:Kimura), J6 3014780-A (a published, but not yet examined, Japanese patent application). Additionally, auxiliary bases have been used together with large excesses of macrocycle to obtain the mono-N-alkylation product by M. Studer et al., *supra*. Purification of the desired mono-N-alkylated product from the large excess of starting material and inorganic salt is a major problem associated with these methods. Additionally, the cost associated with employing a large excess of expensive reagent is prohibitive.

Other mono-N-alkylation attempts by F. Wagner et al., *Inorg. Chem.* 15, 408 (1976) involve selective deprotonation of a transition metal complex of a polyazamacrocycle with strong base followed by alkylation with methyl iodide. Further synthetic manipulation of this compound necessitates metal removal and purification which can be tedious.

Additional synthetic routes which afford mono-N-functional polyazamacrocycles involve lengthy, protection, functionalization, deprotection schemes which are divergent and not always general. For example, see P. S. Pallavincini et al., *J. Amer. Chem. Soc.* 109, 5139–44 (1987) and published European patent application 0 232 751 (1984).

In light of these limitations on mono-N-alkylation techniques existing in the art, it would be desirable to employ a direct alkylation approach which would not be reliant upon the use of excess macrocycle and an auxiliary base and yet would be selective for the desired mono-N-alkylated product.

Surprisingly, the present invention provides a process for preparing selectively the mono-N-alkylated products in a range of solvents without the use of large excesses of macrocycle and auxiliary base. The present process involves reacting between about one to five equivalents of a free base polyazamacrocycle with an appropriate electrophile in a solvent which will not promote a proton transfer.

SUMMARY OF THE INVENTION

The present invention is directed to a novel process for preparing a mono-N-alkylated polyazamacrocycle which comprises reacting an electrophile with between about one and five equivalents of a polyazamacrocycle in a solvent which will not promote a proton transfer. This process results in a greater selectivity for the desired mono-N-alkylated product compared to the bis, tris, tetra or higher N-alkylated products. The difficult and time consuming procedure of separating the excess starting material from the desired product and the commensurate cost involved in doing so is reduced when the essential features of this invention are used: (a) the possible and preferred use of about a one to one equivalent of electrophile to polyazamacrocycle and (b) the range of solvents possible to obtain the mono-N-alkylated product.

DETAILED DESCRIPTION OF THE INVENTION

The present invention concerns the reaction of an appropriate electrophile (E) with a free base polyazamacrocycle (M) in a relatively non-polar, preferably aprotic solvent. The ratio of E to M is about one to five equivalents, preferably from about one to about three equivalents, more preferably from about one to about two equivalents, and most preferably from about one to about one equivalents.

The present process is very general and can produce selective mono-N-alkylation products with various polyazamacrocycles and electrophilies. A slight excess of polyazamacrocycle is preferred to insure complete conversion of the electrophile: however, only small differences in isolated yield occur when larger excesses of the polyazamacrocycle are used.

The term "polyazamacrocycles" as used in the present invention must contain at least two nitrogen atoms and at least one additional hetero atom and a methylene moiety, $(-CH_2)_n$, where n is from 2–4, as a spacer between the hetero atoms. The methylene moiety is independently selected between any two hetero atoms. The term "hetero atom" means a nitrogen, sulfur, or oxygen atom. Examples of polyazamacrocycles containing hetero atoms in addition to nitrogen are polyoxazamacrocycles or polythioazamacrocycles. Also included in the term polyazamacrocycles are any symmetrical rings such as polyazamacrocycle, azaoxamacrocycle or bicyclopolyazamacrocycle (i.e. bridged moieties or fused rings, but the mono-N-alkylation reaction occurs on the nitrogen atom of a saturated ring) which bears secondary amines capable of mono-N-alkylation. Preferably the secondary amines are all chemically equivalent. The macrocycle preferably has a plane of symmetry and the total number of hetero atoms (O, S, N) should preferably total an even integer. The combined total of hetero and carbon atoms in the polyazamacrocycle is preferably 12, 13, or 14. The term polyazamacrocycles means all of these heterocyclic possibilities and includes, for example, 1,3,7-triazacyclononane, 1,4,7,10-tetraazacyclododecane, 1,4,8,11-tetraazacyclotetradecane, 1,4,7,10,13-pentaazacyclopentadecane, 1,4,7,10,13,16-hexaazacyclooctadecane, 1,7,13-triaza-4,10,16-trioxacyclooctadecane, 1,7-diaza-4,10-dithiacyclododecane and the like.

The electrophile (RX) used in the present process is one capable of accepting a pair of electrons from one of the nitrogen atoms in the polyazamacrocycle. A covalent bond results from the reaction between the electrophile and polyazamacrocycle and selective mono-N-alkylation results. In the term RX, the R term is a $C_1$–$C_4$ alkyl; a $C_1$–$C_4$ alkyl which is substituted with a cyano, pyridinyl, $CO_2R^1$ or $CON(R^1)_2$ moiety where $R^1$ is H or $C_1$–$C_4$ alkyl; or an alkylaryl where the alkyl portion is $C_1$–$C_4$ and the aryl portion can be a 5 or 6 member carbon ring or a 9 member ring containing carbon and one or more hetero atoms selected from sulfur, nitrogen or oxygen. The X term is any leaving group. Such leaving groups are well known in the art such as, for example, chloro, bromo, iodo, acetate, trifluoroacetate, triflate, mesylate, diazo, brosylate and the like. Some suitable electrophiles are, for example, d,l-2-bromo-4-N-phthalamidobutanoic acid isopropyl ester, d,l-2-bromo-4-(4-nitrophenyl)butanoic acid isopropyl ester, d,l-2-bromo-4-(4-nitrophenyl)butanoic acid methyl ester, 4-nitrocinnamyl bromide, 4-nitrophenethyl bromide, 4-nitrobenzyl bromide, benzyl bromide and the like.

Concentration of the reagents is not critical for the present process but for economic reasons and reasonable reaction times, the present process is preferably conducted under non-dilution conditions such as $1 \times 10^{-3}$M to 2M in each reagent. Mono-N-alkylations conducted under these concentrations afford the desired product in good to excellent yield with unexpectedly high selectivities. The mono-N-alkylated polyazamacrocycle is obtained in a selectivity of at least 40%, preferably from about 50 to about 98%, compared to the bis, tris and/or tetra N-alkylated products. The following schematic of p-nitrobenzyl bromide reacting with 1,4,7,10-tetraazacyclododecane illustrates what is meant by a mono, bis and tris alkylated product. While not wishing to be bound by theory, obtaining a predominantly mono-N-alkylated product is not expected if similar alkylation rates (e.g. kinetics) for the remaining nitrogens of the azamacrocycle are comparable to the rate constant for the first alkylation.

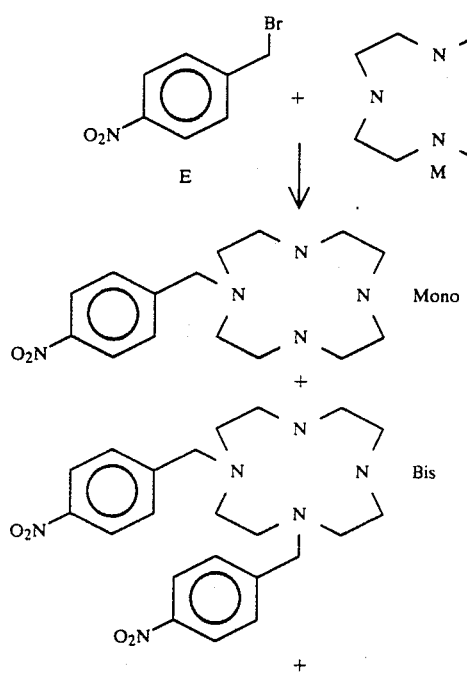

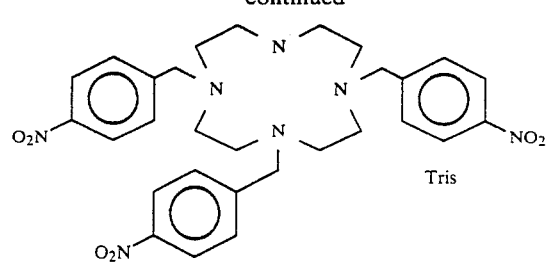

The solvent used for the present process is one which will not promote a proton transfer. Examples of suitable solvents which do not promote a proton transfer are (a) a polar, aprotic solvent: (b) a non-polar, aprotic solvent: or (c) a protic alcohol. Examples of suitable polar, aprotic solvents are, for example, chloroform ($CHCl_3$), methylene chloride ($CH_2Cl_2$), tetrahydrofuran, acetonitrile, 1,4,-dioxane or the like. Examples of suitable non-polar, aprotic solvents are, for example, carbon tetrachloride ($CCl_4$), toluene, benzene, cyclohexane, n-hexane or the like. Examples of suitable protic alcohols are, for example, n-butanol, t-butanol, isopropanol, n-hexanol or the like. The term "aprotic" means that the solvent does not donate a proton to the reaction under the present process conditions. The term "protic alcohol" means a solvent which does not donate a proton to the reaction under the present process conditions although it contains a hydrogen attached to oxygen. The term "non-polar" means that the solvent possesses substantially little dipole moment, i.e., a dipole moment of less than 0.2 debyes.

Temperature employed is in the range of from about $-78°$ C. to about 100° C., preferably from about $-25°$ C. to about 40° C., more preferably from about 0° C. to about 25° C. The time of the reaction, at a temperature of from about 0° C. to about 25° C., is from about 10 to 24 hours. The time of the reaction will vary inversely with the temperature; however, the lower temperatures are preferred to aid in selectivity of the desired mono-N-alkylated product.

The absence of base from the displacement conditions of the reaction helps to prevent epimerization of chiral electrophillic reagents. Hence, optically active mono-N-alkylated adducts are potentially available by this present process. The product formed will possess the inverted optical form from the starting electrophile reagent. For example, the resulting mono-N-alkylated polyazamacrocycle product has the opposite optical configuration from the optically active α-haloacid ester.

The present process does not require the presence of an auxiliary base. Although trace amounts of such bases may be used, the process is conducted in the substantial absence of an inorganic auxiliary base such as, for example, sodium hydroxide, lithium hydroxide, potassium hydroxide, sodium carbonate, potassium carbonate and the like, or of an organic auxiliary base such as, for example, triethylamine, trimethylamine, pyridine, 4-N,N-diethylaminopyridine, diazobicyclododecane, diazobicyclononane and the like.

Furthermore, the absence of strong base and a low temperature allows' for incorporation of other latent functionalities into the periphery of the polyazamacrocyole. For example, both ester and phthalamido functionalities are tolerant of the mild conditions of the present process. A procedure in the art [M. Studer et al., Helv. Chim. Acta. 69, 2081–86 (1986)] which employs lithium hydroxide in polar protic solvents such as aqueous ethanol or methanol may be expected to hydrolyze these groups.

The present process has been used to make valuable synthetic precursors to bifunctional chelator molecules for radioactive pharmaceuticals. [See our copending U.S. application Ser. No. 211,496 by S. Baughman et al., the disclosure of which is hereby incorporated by reference, our copending U.S. application Ser. No. 284,876 by J. Simon et al., the disclosure of which is hereby incorporated by reference, and our copending U.S. application Ser. No. 65,739 by W. J. Kruper et al., the disclosure of which is hereby incorporated by reference.] The brevity of the five step synthetic approach to these compounds, of which the present mono-N-alkylation step is critical, is superior to the nine step process for other pharmaceutical products. See, for example, M. K. Moi et al., J. Amer. Chem. Soc. 110, 6266–27 (1988).

The mono-N-alkylation process of this invention depends upon the availability of the desired electrophile. In the case of substituted α-haloacid esters, commercially available acids may be brominated and converted to an ester in a one pot, two step procedure using N-bromosuccinimide [see D. N. Harpp et al., J. Org. Chem. 40, 3420–27 (1975)]. This ionic bromination procedure is superior to the standard Hell-Vollard-Zelinski process and allows for exclusive alpha halogenation of alkanoic acids which contain even reactive benzyl groups. Optically active α-haloacids are readily available from the corresponding amino acids using recent advances in diazotization chemistry [see B. Koppenhoefer et al., "Organic Synthesis", Vol. 66, Ed. C. Heathcock, Pub. Wiley-Interscience, N.Y., pp. 151–57 (1988)]. Other electrophiles used in this invention may be prepared by procedures known in the art or can be purchased commercially.

The polyazamacrocycles such as 1,4,7,11-tetraazacyclododecane and similar cryptand ligands may be prepared by well documented methods which utilize a template effect in a multi-step procedure. For example see T. S. Adkins et al., J. Amer. Chem. Soc. 96, 2268–70 (1974). With advent of this versatile procedure, a number of these symmetrical macrocycles are now commercially available.

The invention will be further clarified by consideration of the following examples, which are intended to be purely exemplary of the use of this invention.

General Experimental

In the following examples, the equipment used was as follows:
Mass spectra were obtained on either a Finnigan TSQ mass spectrometer or a VG ZAB-MS high-resolution mass spectrometer:
$^1$H and $^{13}$C NMR spectra were obtained using a Varian VXR-300 spectrometer; and
IR were recorded on a Nicolet SSX FT/IR instrument.

In the following examples, all solvents were Fisher HPLC grade materials. All preparative chromatography of organic compounds was performed using flash chromatography techniques by W. C. Still et al., J. Org. Chem. 43, 2923–2925 (1978) and employed the following solvent systems:
Solvent System 1—CHCl$_3$:CH$_3$OH:conc. NH$_4$OH 2:2:1 (V:V:V);
Solvent System 2—CHCl$_3$:CH$_3$OH:conc. NH$_4$OH 12:4:1 (V:V:V); and
Solvent System 3—CHCl$_3$:CH$_3$OH:conc. NH$_4$OH 16:4:1 (V:V:V).

R$_f$ values are reported using these solvent systems and commercially available silica plates.

1,4,7,10—Tetraazacyclododecane and 1,4,7,10,13-pentaazacyclopentadecane were purchased from Parrish Chemical Co.

1,4,8,11—Tetraazacyclotetradecane was purchased from Aldrich Chemical Co.

The following terms used in the examples are defined as follows:
conc. means concentrated; and
dec means decomposition.

Preparation of electrophiles

EXAMPLE A

Preparation of d,l-2-bromo-4-(4-nitrophenyl)butanoic acid methyl ester.

To a solution of 5 mL of carbon tetrachloride and 15 mL of thionyl chloride was added 10.46 g (0.05 mole) of 4-(4-nitrophenyl)butanoic acid under a nitrogen atmosphere. The solution was brought to reflux for one hour with initial rapid liberation of hydrogen chloride and sulfur dioxide. Following the gaseous liberation, 11.0 g (0.06 mole) of N-bromo-succinimide in 25 mL of carbon tetrachloride and 3 drops of 48% aqueous hydrogen bromide catalyst was added to the warm solution whereupon bromine liberation occurred. The dark red solution was refluxed for an additional 15 minutes, cooled and poured into 100 mL of methanol with stirring. TLC (60:40 ethyl acetate:n-hexane) indicated a product characterized by R$_f$=0.69. The excess solvent was removed and the dark red oil was filtered through a flash silica gel pad 1 in. × 6 in. (2.5 cm × 15.2 cm) using methylene chloride as the eluent. Evaporation of solvent gave 14.5 g of a colorless oil which was an 85:15 mixture of the title product:methyl ester of the starting material and was further characterized by:
$^1$H NMR (CDCl$_3$)
δ8.16(d), 7.38(d), 4.20(dd), 3.79(s), 2.88(m);
$^{13}$C NMR (CDCl$_3$)
δ169.6, 147.5, 129.3, 123.7, 53.0, 44.4, 35.5, 33.0.

EXAMPLE B

Preparation of d,l-2-bromo-4-(4-nitrophenyl)butanoic acid isopropyl ester.

The title ester was obtained as a clear oil in 50% yield after quenching the crude acid chloride with isopropanol and chromatographic purification. The product (R$_f$=0.73, methylene chloride) was devoid of any unbrominated ester and was further characterized by:
$^1$H NMR (CDCl$_3$)
δ8.16(d), 7.38(d), 5.05(septet), 4.14(dd), 2.88(m), 2.39(m), 1.29(d);
$^{13}$C NMR (CDCl$_3$)
δ168.7, 147.7, 129.3, 123.8, 69.9, 45.1, 35.6, 33.0, 21.5, 21.2.

EXAMPLE C

Preparation of trans-p-nitrocinnamyl bromide.

In 35 mL of dry acetonitrile under nitrogen atmosphere was added 7.3 g (27.9 mmole) of triphenylphosphine. To the solution was added dropwise over 15 minutes 4.31 g of bromine (27.0 mmole) while cooling the reaction mixture to maintain the temperature between 0°–10° C. The solution was allowed to warm to room temperature (about 22°–25° C.) and 5.0 g (27.9 mmole) of p-nitrocinnamyl alcohol (Pfaultz & Bauer Chemical Co.) was added as a slurry in 50 mL of acetonitrile which caused an exothermic reaction, temperature about 45° C. The resulting dark red solution was heated for one hour at 60° C. with stirring and then poured into 500 mL of ether. Triphenylphosphine oxide precipitated from the solution after standing overnight (about 16 hours). The solution was filtered and 15 g of flash silica gel was added to the solution, followed by solvent removal. The resulting powder matrix was applied to a 3 in.×8 in. (7.6 cm×20.3 cm) flash column and the desired product was eluted with hexane, followed by 20% ethyl acetate in hexane to yield 5.8 g (23.9 mmole) of the desired pure trans product in 86% yield (MP=75°–76° C., $R_f$=0.81, 60:40 ethyl acetate:n-hexane) and was further characterized by:

$^1$H NMR (CDCl$_3$)
δ8.17(d), 7.51(d), 6.70(dd), 6.56(dt), 4.16(dd);
$^{13}$C NMR (CDCl$_3$)
δ147.3, 142.1, 132.0, 129.8, 127.2, 123.9, 31.8.

EXAMPLE D

Preparation of d,l-2-bromo-4-(N-phthalamido)-butanoic acid isopropyl ester.

Into a flask equipped with a trap and water condenser was placed 14.8 g (100 mmole) of phthalic anhydride, 10.3 g (100 mmole) of Y-aminobutyric acid (Aldrich Chemical Co.), 1.3 mL of triethylamine and 150 mL of toluene. The mixture was brought to reflux and 1.75 mL of water was removed azeotropically over 1.5 hours. The solution was allowed to cool and stand overnight (about 16 hours). The resulting white crystals that formed were filtered, washed with hexane and dried. The crude crystals were then washed with 250 mL of 5% aqueous hydrogen chloride and 100 mL of cold water. After drying, 19.0 g (81.5 mmole) of 4-(N-phthalamido)butanoic acid was obtained in 82% yield (MP=114.5°–115.5° C., recrystallized from 30% methanol in water) and further characterized by:

$^1$H NMR (CDCl$_3$)
7.84(dd), 7.72(dd), 6.05(bs), 3.77(t), 2.42(t), 2.02(p);
$^{13}$C NMR (CDCl$_3$)
δ177.9, 169.4, 134.0, 123.3, 37.1, 31.2, 23.6.

The above prepared 4-(N-phthalamido)butanoic acid was reacted by the procedure of Example A and B to obtain the title ester as a white solid, yield 68%, (MP=72°–4.5° C., $R_f$=0.38, chloroform) after flash silica gel chromatography using chloroform as an eluant, and further characterized by:

$^1$H NMR (CDCl$_3$)
δ7.85(dd), 7.73(dd), 5.04(septet), 4.23(dd), 3.85(dt), 2.51(m), 2.36(m), 1.29(d), 1.26(d).

PROCESS OF THE INVENTION

EXAMPLE 1

Preparation of 1,4,7,10-tetraaza-1-[(4-nitrophenyl)methyl]cyclododecane.

The free base, 3.5 g (20.3 mmoles), of 1,4,7,10-tetraazacyclododecane and 1.7 g (7.87 mmoles) of p-nitrobenzyl bromide (a polyazamacrocycle to electrophile ratio of about 2.5:1) in 50 mL of chloroform were stirred under nitrogen for 24 hours at 25° C. The chloroform slurry of hydrobromide salt was then applied to a 1 in.×17 in. (2.5 cm×43.2 cm) column of flash silica gel (Solvent System 3). The product, 2.13 g (6.93 mmoles) was obtained as a pale yellow solid (MP=128°–29° C., $R_f$=0.58 Solvent System 3) in 88% yield and further characterized by:

$^1$H NMR (CDCl$_3$)
δ8.18(d), 7.49(d), 3.69(s), 2.82(t), 2.70(t), 2.59(m);
$^{13}$C NMR (CDCl$_3$)
δ147.2, 128.4, 123.8, 58.8, 51.7, 47.1, 46.3, 45.1.

EXAMPLE 2

Preparation of 1,4,7,10-tetraaza-1-[2-(4-nitrophenyl)ethyl]cyclododecane.

To a stirred solution of 3 5 g (20.3 mmole) of 1,4,7,10-tetraazacyclododecane in 50 mL of pentene stabilized chloroform was added dropwise over five minutes with vigorous stirring under a nitrogen atmosphere 4.0 g (17.4 mmoles) of 1-bromo-2-(4-nitrophenyl)ethane (Aldrich Chemical Co.). This constituted a polyazmacrocycle to electrophile ratio of about 1.2:1. The stirring was continued overnight at about 25° C. whereupon crystals of amine hydrobromide precipitated from solution. The contents of the flask were applied to a flash silica gel column 1 in.×18 in. (2.5 cm×45.7 cm) which had been pre-eluted with 5% methanol in chloroform and 200 mL of this solution was applied as an eluent, followed by elution with Solvent System 3. The p-nitrostyrene (1.45 g, 9.7 mmole, $R_f$=0.98, Solvent System 2) was cleanly separated from 2.27 g (7.06 mmole) of the desired product as an orange yellow oil (yield 40.6%) which solidified upon standing ($R_f$=0.73, Solvent System 2). A sample was recrystallized [MP=146.5°–148.5° C. (dec)] from chloroform/cyclohexane and was further characterized by:

$^1$H NMR (CDCl$_3$)
δ8.14(d), 7.40(d), 2.91(t), 2.77(t), 2.72(t), 2.50(t), 2.60(s);
$^{13}$C NMR (CDCl$_3$)
δ148.5, 129.6, 123.4, 55.5, 51.4, 46.9, 45.9, 45.1, 33.7.

EXAMPLE 3

Preparation of 1,4,7,10-tetraaza-1-[1-carbomethoxy-3-(4-nitrophenyl)propyl]cyclododecane.

To a stirred solution of 1.72 g (10.0 mmole) of 1,4,7,10-tetraazacyclododecane in 17 mL of pentene stabilized chloroform was added 2.07 g (5.82 mmole) of crude d,l-2-bromo-4-(4-nitrophenyl)butanoic acid methyl ester (prepared by the procedure of Example A) over a five minute period under a nitrogen atmosphere. This constituted a polyazamacrocycle to electrophile ratio of about 1.7:1. The reaction mixture was stirred for 48 hours at about 25° C. and TLC (Solvent System 2) indicated the conversion to the desired monoalkylation product ($R_f$=0.73, ninhydrin, iodine, and UV active). The yellow chloroform solution was applied to a 1 in.×16 in. (2.5 cm×40.6 cm) flash silica gel column which had been preeluted with 5% methanolic chloroform, followed by elution with 250 mL of the preelution solvent system, and then elution with Solvent System 2. The fractions containing the desired product were combined and evaporated affording 2.15 g (5.46 mmole) of the desired.. product (MP=156°–159° C., recrystallized from chloroform, ether) in 94% yield and further characterized by:

$^1$H NMR (CDCl$_3$)
δ8.14(d), 7.39(d), 3.71(s), 3.39(dd), 2.5–3.0(m), 2.08(m), 2.01(m);
$^{13}$C NMR (CDCl$_3$)

δ172.7, 149.3, 146.4, 129.2, 123.6, 62.3, 51.2, 48.9, 47.2, 45.8, 45.4, 32.8, 30.9.

3450, 2860, 1735, 1350, 915.

EXAMPLE 4

Preparation of 1,4,7,10,13-pentaaza-1-[1-carboisopropoxy-3-(4-nitrophenyl)propyl]-cyclopentadecane.

By the procedure of Example 3, one equivalent of 1,4,7,10,13-cyclopentadecane was reacted with one equivalent of d,l-2-bromo-4-(4-nitrophenyl) butanoic acid isopropyl ester. This constituted a polyazamacrocycle to electrophile ratio of about 1:1.

The purified desired product was obtained as a light yellow oil in 77% yield after chromatography on silica gel ($R_f$=0.82, Solvent System 2) and further characterized by:

$^1$H NMR (CDCl$_3$)
δ8.14(d), 7.49(d), 5.09(septet), 4.86(s), 3.38(dd,s), 2.5–3.0(m), 2.30(m), 2.11(m), 1.29(d);

$^{13}$C NMR (CDCl$_3$)
δ171.9, 149.1, 146.5, 129.5, 123.6, 68.7, 61.9, 49.5, 46.8, 46.7, 45.5, 45.3, 32.9, 32.1, 22.1, 22.0;

IR (CDCl$_3$) cm$^{-1}$

EXAMPLE 5

Yields of mono-N-alkylation of p-nitrobenzyl bromide (Aldrich Chemical Co.) with 1,4,7,10-tetraazacyclododecane are given in Table 1. The results clearly show the mono-N-alkylated product is obtained preferentially over the bis and tris alkylated products and that the ratio of M:E is from about 1:1 to 1:2.

TABLE I

| Ex. No. | M:E | [E] MOLARITY | SOLVENT | % ISOLATED YIELD** | | | MONO:BIS |
| --- | --- | --- | --- | --- | --- | --- | --- |
| | | | | MONO | BIS | TRIS | |
| 5A | 1:1.0 | 1 | CHCl$_3$ | 49 | 11 | 5 | 4.5:1 |
| 5B | 1:1.5 | 1 | CHCl$_3$ | 66 | 10 | 3 | 6.6:1 |
| 5C | 1:1.5 | 4 × 10$^{-2}$ | CHCl$_3$ | 73 | 9 | 2 | 7.4:1 |
| 5D | 1:1.5 | 1 | CH$_3$OH | 39 | 16 | 3 | 2.4:1 |
| 5E | 1:1.5 | 1 | CH$_3$(CH$_2$)$_3$OH | 43 | 15 | 3 | 3.0:1 |
| A* | 1:1.5 | 1 | CH$_3$OH*** | 34 | 19 | 7 | 1.8:1 |

*A is not a process of the invention.
**Isolated yield of product after flash chromatography; process at 25° C.
***1.0 equivalents of KCO$_3$ added relative to bromide.

EXAMPLE 6

Preparation of various mono-N-alkylpolyazamacrocycles using the process of the invention.

In Table II following, various electrophiles were reacted with polyazamacrocycles which gave yields greater than 40% selectivity for the desired mono-N-alkylpolyazamacrocycle, expressed as percent (%) isolated yield. The process was run using the equivalents and solvents given in Table II and by the procedure of Examples 1–4. Table III following indicates the structure of the desired mono-N-alkylpolyazamacrocycle formed by the reaction in Table II.

TABLE II

| EX. | ELECTROPHILE | MACROCYCLE (EQ) | SOLVENT | % ISOLATED YIELD* | MONO:BIS |
| --- | --- | --- | --- | --- | --- |
| 6A | O$_2$N–C$_6$H$_4$–CH$_2$Br | pentaaza-macrocycle (2.0) | CHCl$_3$ | 100 | |
| 6B | O$_2$N–C$_6$H$_4$–CH$_2$Br | tetraaza-macrocycle (1.0) | CHCl$_3$ | 50 | 4.5:1 |
| 6C | O$_2$N–C$_6$H$_4$–CH$_2$Br | triaza-macrocycle (2.0) | CHCl$_3$ | 87 | 10:1 |
| 6D | O$_2$N–C$_6$H$_4$–CH$_2$CH$_2$Br | tetraaza-macrocycle (1.1) | CHCl$_3$ | 43** | >20:1 |

TABLE II-continued

| EX. | ELECTROPHILE | MACROCYCLE (EQ) | SOLVENT | % ISOLATED YIELD* | MONO:BIS |
|---|---|---|---|---|---|
| 6E | 4-O2N-C6H4-CH2CH2-CHBr-CO2CH3 | cyclam (1.0) | CHCl3 | 81 | |
| 6F | 4-O2N-C6H4-CH2CH2-CHBr-CO2CH3 | cyclam (1.7) | CHCl3 | 94 | |
| 6G | 4-O2N-C6H4-CH2CH2-CHBr-CO2CH3 | cyclam (1.7) | CCl4 | 70 | |
| 6H | 4-O2N-C6H4-CH2CH2-CHBr-CO2CH3 | cyclam (1.7) | THF | 86 | |
| 6I | 4-O2N-C6H4-CH2CH2-CHBr-CO2CH3 | hexaazamacrocycle (1.5) | CHCl3 | 61 | |
| 6J | 4-O2N-C6H4-CH2CH2-CHBr-CO2CH(CH3)2 | hexaazamacrocycle (1.5) | CHCl3 | 64 | |
| 6K | C6H5-CH2Cl | cyclam (1.2) | CHCl3 | 58 | |
| 6L | 4-O2N-C6H4-CH=CH-CH2Br | cyclam (1.2) | CHCl3 | 69 | 4.1:1 |

TABLE II-continued
| EX. | ELECTROPHILE | MACROCYCLE (EQ) | SOLVENT | % ISOLATED YIELD* | MONO:BIS |
|---|---|---|---|---|---|
| 6M | 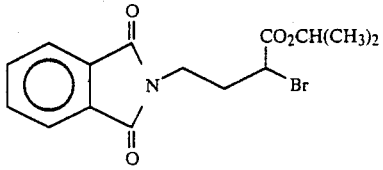 | 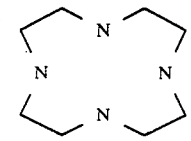 (1.1) | $CHCl_3$ | 83 | 34:1 |
*Flash chromatography purification based upon electrophile as limiting reagent (1.0 eq.)
**p-nitrostyrene isolated in 54% yield
TABLE III
| EX. | POLYAZAMACROCYCLE |
|---|---|
| 6A | 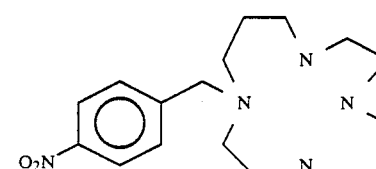 |
| 6B AND 6C | 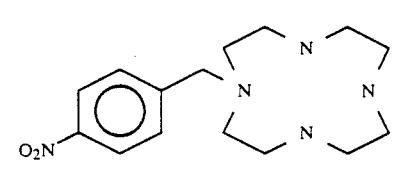 |
| 6D | 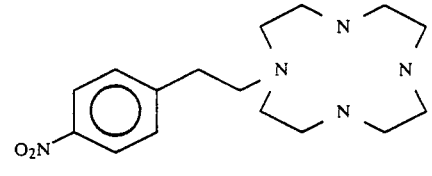 |
| 6E, 6F, 6G AND 6H | 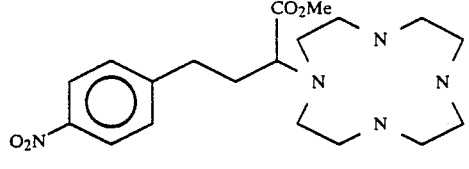 |
| 6I | 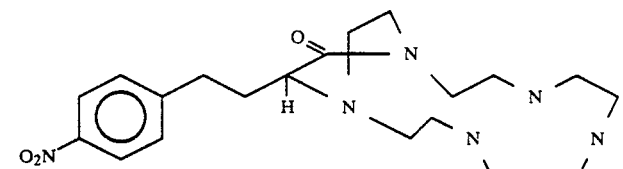 |
| 6J | 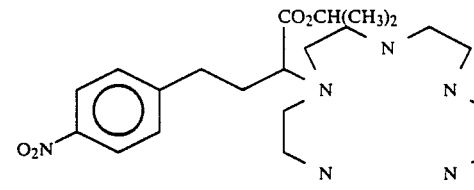 |

TABLE III-continued

| EX. | POLYAZAMACROCYCLE |
|---|---|
| 6K | benzyl-substituted polyazamacrocycle (phenyl-CH2- attached to tetraazacyclododecane ring) |
| 6L | 4-nitrocinnamyl-substituted polyazamacrocycle (O2N-C6H4-CH=CH-CH2- attached to tetraazacyclododecane ring) |
| 6M | phthalimido-substituted polyazamacrocycle with CO2CH(CH3)2 group (phthalimide-N-CH2CH2-CH(CO2CH(CH3)2)- attached to tetraazacyclododecane ring) |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims:

What is claimed is:

1. A process for preparing a mono-N-alkylated polyazamacrocycle consisting essentially of reacting an electrophile with between about one and three equivalents of a polyazamacrocycle in a solvent which will not promote a proton transfer and recovery of the thus prepared mono-N-alkylated polyazamacrocycle; wherein the electrophile is represented by the formula RX wherein R is a $C_1$-$C_4$ alkyl; a $C_1$-$C_4$ alkyl which is substituted with a cyano, pyridinyl, $CO_2R^1$ or $CON(R^1)_2$ moiety where $R^1$ is H or $C_1$-$C_4$ alkyl; or an alkylaryl where the alkyl portion is $C_1$-$C_4$ and the aryl portion is a 5 or 6 member carbon ring or a 9 member ring containing carbon and one or more hetero atoms selected from sulfur, nitrogen or oxygen and X is chloro, bromo, iodo, acetate, trifluoroacetate, triflate, mesylate, diazo or brosylate; and wherein the polyazamacrocycle contains at least two nitrogen atoms and at least one additional hetero atom selected form the group consisting of oxygen sulfur and nitrogen, and a methylene moiety, $(-CH_2-)_n$, where n is from 2-4, as a spacer between the hetero atoms such that the total carbon and hetero atoms in the polyazamacrocycle is 12, 13 or 14.

2. A process of claim 1 wherein the solvent is a non-polar, aprotic solvent: a polar, aprotic solvent: or a protic alcohol.

3. The process of claim 2 wherein the solvent is a non-polar, aprotic solvent.

4. The process of claim 3 wherein the solvent is carbon tetrachloride, toluene, benzene, cyclohexane or n-hexane.

5. The process of claim 2 wherein the solvent is a polar, aprotic solvent.

6. The process of claim 5 wherein the solvent is chloroform, methylene chloride, tetrahydrofuran, acetonitrile or 1,4-dioxane.

7. The process of claim 6 wherein the solvent is chloroform.

8. The process of claim 2 wherein the solvent is a protic alcohol.

9. The process of claim 8 wherein the solvent is n-butanol, t-butanol, isopropanol, or n-hexanol.

10. The process of claim 1 wherein the polyazamacrocycle contains at least two nitrogen atoms and at least one additional hetero atom and a methylene moiety, $(-CH_2-)_n$, where n is from 2-4, as a spacer between the hetero atoms.

11. The process of claim 1 wherein the polyazamacrocycle is symmetrical.

12. The process of claim 1 wherein the polyazamacrocycle is 1,4,7,10-tetraazacyclododecane, 1,4,8,11-tetraazacyclotetradecane, or 1,7-diaza-4,10-dithiacyclododecane.

13. The process of claim 1 wherein the electrophile is d,l,-2-bromo-4-N-phthalamidobutanoic acid isopropyl ester, d,l-2-bromo-4-(4-nitrophenyl) butanoic acid isopropyl ester, d,l-2-bromo-4-(4-nitrophenyl)butanoic acid methyl ester, 4-nitrocinnamyl bromide, 4-nitrophenethyl bromide, 4-nitrobenzyl bromide, or bensyl bromide.

14. The process of claim 1 wherein R is an optically active α-haloacid ester.

15. The process of claim 14 wherein the resulting mono-N-alkylated polyazamacrocycle product has the opposite optical configuration from the optically active α-haloacid ester.

16. The process of claim 1 wherein the temperature is from about −78° C. to about 100° C.

17. The process of claim 16 wherein the temperature is from about −25° C. to about 40° C.

18. The process of claim 17 wherein the temperature is from about 0° C. to about 25° C.

19. The process of claim 1 wherein between about one and about two equivalents of polyazamacrocycle are used relative to the electrophile.

20. The process of claim 1 wherein about one equivalent of polyazamacrocycle is used relative to the electrophile.

21. The process of claim 1 wherein the mono-N-alkylated polyazamacrocycle is obtained in a selectivity of at least 40%.

22. The process of claim 1 wherein the mono-N-alkylated polyazamacrocycle is obtained in a selectivity of from about 50 to about 98%.

* * * * *

UNITED STATES PATENT AND TRADEMARK OFFICE
CERTIFICATE OF CORRECTION

PATENT NO. : 5,064,956

DATED : November 12, 1991

INVENTOR(S) : William J. Kruper, Jr.

It is certified that error appears in the above-identified patent and that said Letters Patent is hereby corrected as shown below:

Column 15, line 49, "selected form" should correctly appear as -- selected from --.

Column 15, line 56, "solvent: a polar, aprotic solvent:" should correctly appear as -- solvent; a polar, aprotic solvent; --.

Column 16, line 43, "bensyl" should correctly appear as -- benzyl --.

Signed and Sealed this

Twenty-second Day of June, 1993

Attest:

MICHAEL K. KIRK

*Attesting Officer*   *Acting Commissioner of Patents and Trademarks*